(12) United States Patent
Zhao et al.

(10) Patent No.: US 11,401,233 B1
(45) Date of Patent: Aug. 2, 2022

(54) PLEUROMUTILIN SALICYLIC ACID ESTER WITH ANTIBACTERIAL ACTIVITY AND A METHOD OF PREPARING THE SAME

(71) Applicants: Qianqian Zhao, Xi'an (CN); Liang Xin, Xi'an (CN); Jingyi Li, Xi'an (CN); Ruina Bian, Xi'an (CN); Dan Yang, Xi'an (CN); Liang Qi, Xi'an (CN); Bin Tian, Xi'an (CN); Jian Zha, Xi'an (CN); Wenbo Yao, Xi'an (CN); Gennian Mao, Xi'an (CN); Han Li, Xi'an (CN); Chunyang Shi, Xi'an (CN); Yongbo Wang, Xi'an (CN); Jingwen Xu, Xi'an (CN)

(72) Inventors: Qianqian Zhao, Xi'an (CN); Liang Xin, Xi'an (CN); Jingyi Li, Xi'an (CN); Ruina Bian, Xi'an (CN); Dan Yang, Xi'an (CN); Liang Qi, Xi'an (CN); Bin Tian, Xi'an (CN); Jian Zha, Xi'an (CN); Wenbo Yao, Xi'an (CN); Gennian Mao, Xi'an (CN); Han Li, Xi'an (CN); Chunyang Shi, Xi'an (CN); Yongbo Wang, Xi'an (CN); Jingwen Xu, Xi'an (CN)

(73) Assignee: SHAANXI UNIVERSITY OF SCIENCE AND TECHNOLOGY, Xi'an (CN)

(*) Notice: Subject to any disclaimer, the term of this patent is extended or adjusted under 35 U.S.C. 154(b) by 0 days.

(21) Appl. No.: 17/175,582

(22) Filed: Feb. 12, 2021

(51) Int. Cl.
  *C07C 69/88* (2006.01)
  *C07C 67/08* (2006.01)
  *C07C 67/14* (2006.01)
(52) U.S. Cl.
  CPC .............. *C07C 69/88* (2013.01); *C07C 67/08* (2013.01); *C07C 67/14* (2013.01)

(58) Field of Classification Search
  None
  See application file for complete search history.

(56) References Cited

U.S. PATENT DOCUMENTS

| 11,117,859 B1 * | 9/2021 | Yang | ..................... C07C 233/83 |
| 11,155,514 B1 * | 10/2021 | Tian | ..................... C07C 69/736 |

(Continued)

FOREIGN PATENT DOCUMENTS

| CN | 102180809 | * | 9/2011 |
| WO | WO0027790 | * | 5/2000 |

OTHER PUBLICATIONS

Fazakerley ("Synthesis and synthetic chemistry of pleuromutilin" Tetrahedron, 70, 2014, p. 6911-6930) (Year: 2014).*
CAS registry No. 125-65-5 (Year: 1984).*

*Primary Examiner* — Amy C Bonaparte

(57) ABSTRACT

A compound with anti-drug resistant bacteria activity having the following formula (I):

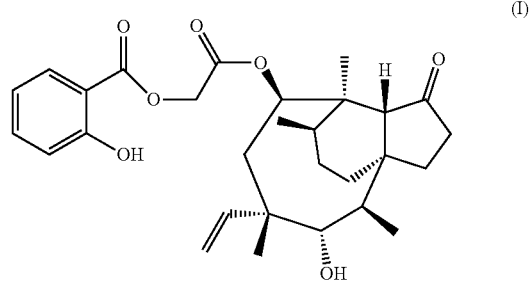

(I) is disclosed. The methods of preparing the compound of formula (I) are also disclosed.

16 Claims, 2 Drawing Sheets

(56) References Cited

U.S. PATENT DOCUMENTS 11,168,049 B1 * 11/2021 Tang ................ C07C 69/732
11,186,607 B1 * 11/2021 Tang .................. C07J 9/005

* cited by examiner

PLEUROMUTILIN SALICYLIC ACID ESTER WITH ANTIBACTERIAL ACTIVITY AND A METHOD OF PREPARING THE SAME

FIELD OF THE INVENTION

The present invention relates to the field of medicinal chemistry, and in particular, to pleuromulin salicylic acid ester with anti-drug resistant bacteria activity and a method of preparing the same.

BACKGROUND OF THE INVENTION

Antimicrobials are the most commonly used drugs for the treatment of bacterial infections. Over the years, with the popularity and application of antibiotics around the world, as well as serious unreasonable abuse, a variety of drug-resistant strains have appeared in both Gram-positive and Gram-negative bacteria. Among them, the problem of drug resistance of Gram-positive bacteria is particularly serious. Methicillin-resistant *Staphylococcus aureus* and *Staphylococcus epidermidis*, penicillin-resistant *Streptococcus pneumoniae* and vancomycin-resistant enterococci are serious clinical problems. At present, there is a lack of effective drugs for the infection caused by these drug-resistant bacteria. There is an urgent need to develop new structural antimicrobials without cross-resistance and more effective.

Pleuromulin (compound of formula II) belongs to tricyclic diterpenoid antibiotics. The main structure for its antibacterial effect is the tricyclic skeleton in the compound, which can form an inducing fit effect with the peptide acyltransferase active center (PTC) of the 50S subunit of the bacterial ribosome. Pleuromutilin antibiotics have certain antibacterial activity against most Gram-positive bacteria except *Enterococcus faecalis*. In addition, pleuromutilin antibiotics also have good in vitro antibacterial effects against fastidious gram-negative bacteria including *Haemophilus influenzae*, *Moraxella catarrhalis* and *Neisseria* spp. It has been more than half a century that pleuromutilin antibiotics have been discovered. Although the application of these drugs in veterinary clinics has achieved considerable results, there is no pleuromutilin antibiotics available for systemic medicine in the human medicine clinic.

Salicylic acid (compound of formula IV) is a plant willow bark extract and a natural anti-inflammatory drug. The commonly used cold medicine aspirin is sodium acetylsalicylate, a derivative of salicylic acid. Sodium p-aminosalicylate (PAS) is a commonly used anti-tuberculosis drug. Salicylic acid is often used in dermatology to treat various chronic skin diseases, such as acne. Salicylic acid can remove hominess, sterilization and anti-inflammation, so it is very suitable for the treatment of acne caused by clogged pores. International mainstream acne products are hydrated salicylic acid, and the concentration is usually 0.5-2%.

In the present invention, pleuromulin is combined with salicylic acid to obtain a pleuromulin salicylic acid ester. Preliminary in vitro antibacterial activity experiment shows that the compound has excellent antibacterial activity and anti-drug-resistant bacteria activity.

SUMMARY OF THE INVENTION

In one embodiment, the present invention provides a compound having the following formula (I) (pleuromulin salicylic acid ester):

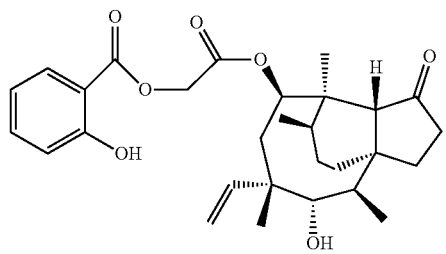

In another embodiment, a method of preparing the compound of formula (I) includes reacting a compound of formula (II) with a compound of formula (III) to obtain the compound of formula (I):

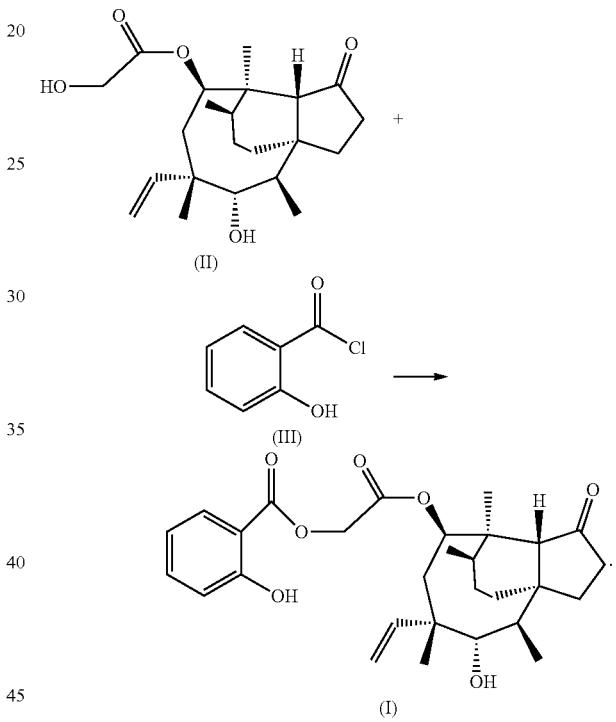

In another embodiment, the reaction of the compound of formula (II) with the compound of formula (III) comprises the following steps: placing the compound of formula (II) and the compound of formula (III), in a molar ratio of 1:1 to 1:1.3, in a reactor; adding an organic solvent and a catalytic amount of triethylamine under nitrogen atmosphere to obtain a reaction mixture; heating the reaction mixture at 20-50° C. for 4-8 hours; concentrating the reaction mixture and extracting with with ethyl acetate to obtain a crude product; and purifying the crude product on a silica gel fresh chromatography column with petroleum ether and ethyl acetate as an eluent to obtain the compound of formula (I).

In another embodiment, the organic solvent is toluene, dichloromethane, or N,N-dimethylformamide.

In another embodiment, the organic solvent is dichloromethane.

In another embodiment, the molar ratio of the compound of formula (II) and the compound of formula (III) is 1:1.1.

In another embodiment, the reaction mixture is heated at 20° C.

In another embodiment, the reaction mixture is heated for 5 hours.

In another embodiment, the eluent is petroleum ether: ethyl acetate=1:1.

In another embodiment, a method of preparing the compound of formula (I) includes reacting a compound of formula (II) with a compound of formula (IV) to obtain the compound of formula (I):

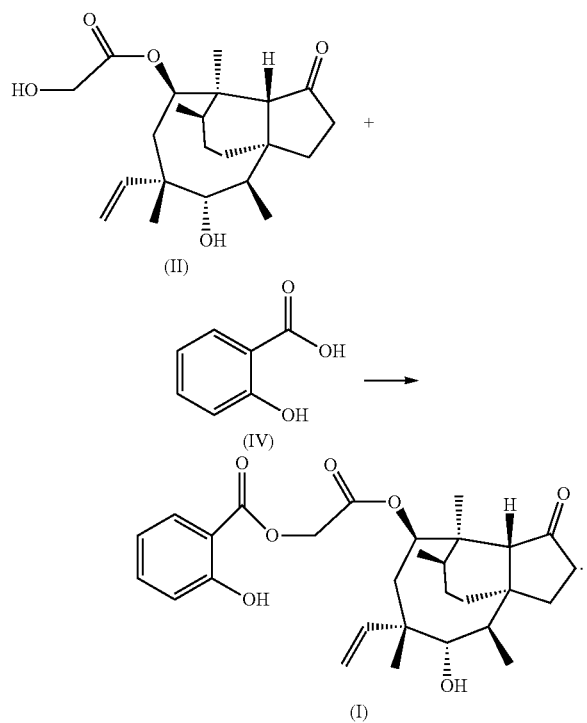

In another embodiment, the reaction of the compound of formula (II) with the compound of formula (IV) comprises the following steps: placing the compound of formula (II), a catalyst, and an ionic liquid in a reactor under nitrogen atmosphere, the catalyst being 12-molybdosilicic acid hydrate ($H_6Mo_{12}O_{41}Si$); adding the compound of formula (IV) to the reactor to form a reaction mixture; heating the reaction mixture at 20-40° C. for 2-5 hours; placing the reaction mixture in a separating funnel to separate a crude product; purifying the crude product by recrystallization in methanol to obtain the compound of formula (I); and recycling the ionic liquid.

In another embodiment, the ionic liquid is 1-octyl-3-methylimidazo-lium hexafluorophosphate, 1-hexyl-3-methylimidazolium tetrafluoroborate, or 1-butyl-3-methylimidazolium tetrafluoroborate.

In another embodiment, the ionic liquid is the ionic liquid is 1-octyl-3-methylimidazo-lium hexafluorophosphate ($C_8H_{15}F_6N_2P$).

In another embodiment, the compound of formula (II) and the compound (IV) have a molar ratio of 1:1 to 1:1.3.

In another embodiment, the molar ratio of the compound of formula (II) and the compound of formula (IV) is 1:1.1.

In another embodiment, the reaction mixture is heated at 25° C.

In another embodiment, the reaction mixture is heated for 3 hours.

It is to be understood that both the foregoing general description and the following detailed description are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention.

In the drawings.

DETAILED DESCRIPTION OF THE ILLUSTRATED EMBODIMENTS

Figure 1:
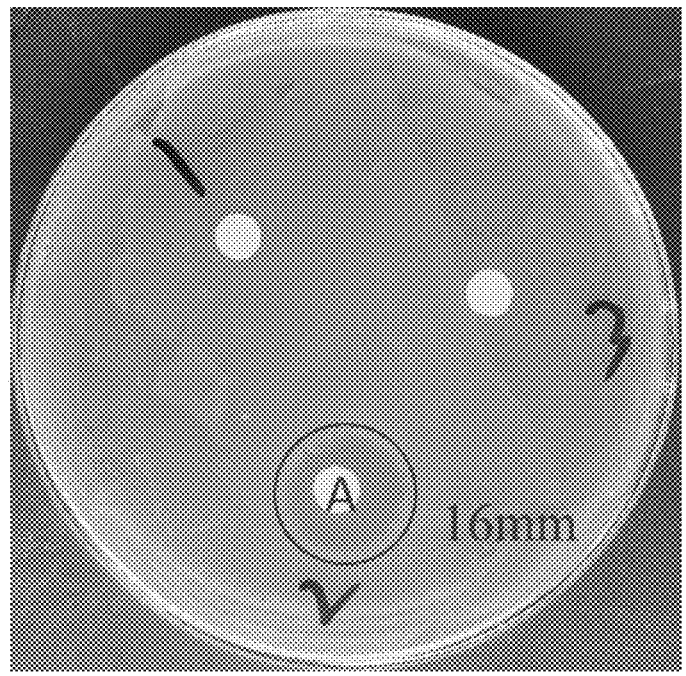
FIG. 1 shows the in vitro antibacterial activity of pleuromulin salicylic acid ester against drug-resistant bacteria MARS 18-171.

Reference will now be made in detail to embodiments of the present invention, example of which is illustrated in the accompanying drawings. The following examples illustrate the present invention, but the present invention is not limited to the following examples.

EXAMPLE 1

Preparation of Compound of Formula (I) (2-(((3aR, 5S,6S,8R,9R,9aR,12R)-5-hydroxy-6,9,12-trimethyl-1-oxo-6-vinyldecahydro-3a,9-propanocyclopenta[8]annulen-8-yl)oxy)-2-oxoethyl 2-hydroxybenzoate)

In a 100 mL three-necked flask, 246.0 mg (0.65 mmol) of pleuromulin and 6.1 mg (0.06 mmol) triethylamine were dissolved in 20 mL of dichloromethane under nitrogen atmosphere. 112.3 mg (0.72 mmol) of salicyloyl chloride (compound of formula III) was dissolved in 10 mL of dichloromethane, and added dropwise to the reaction mixture by a separatory funnel. After the completion of the dropwise addition, the reaction mixture was heated at 20° C. for 5 hours. Thin layer chromatography was used to track the reaction to completion, heating was stopped, and the protective device was removed. The reaction mixture was concentrated, washed with water, and extracted with ethyl acetate. Ethyl acetate was concentrated and dried to obtain a crude product. The crude product was purified by silica gel column chromatography with petroleum ether/ethyl acetate=1:1 as eluent, and the eluent was concentrated under reduced pressure and dried to obtain 221.4 mg of the title compound, a yield of 70.35%.

$^1$H-NMR (400 MHz, chloroform-d) δ (ppm): 8.17(1H, d), 7.97 (1H, d), 7.04 (1H, d), 6.95 (1H, d), 6.55 (1H,d), 6.48 (1H, d), 5.89 (2H, m), 5.34 (2H, d), 4.78 (1H, m) , 4.01 (1H, t), 3.42 (1H, t), 2.36 (1H, s) , 2.30 (2H, m), 2.19 (2H, m), 1.73-1.40 (9H, m), 1.19 (3H, m), 0.94 (3H, d), 0.79 (3H, m); $^{13}$C-NMR (400 MHz, chloroform-d) δ ppm): 216.8, 166.0, 138.8, 136.3, 130.1, 119.4, 117.4, 74.6, 70.6, 58.1, 45.4, 44.7, 44.0, 41.9, 41.5, 36.7, 36.0, 34.4, 30.4, 26.8, 26.3, 24.8, 16.7, 14.8, 11.5.

EXAMPLE 2

Preparation of Compound of Formula (I)

In a 100 mL three-necked flask, 246.0 mg (0.65 mmol) of pleuromulin and 6.1 mg (0.06 mmol) triethylamine were dissolved in 20 mL of N,N-dimethylformamide, under nitrogen atmosphere. 112.3 mg (0.72 mmol) of salicyloyl chloride (compound of formula III) was dissolved in 10 mL of N,N-dimethylformamide, and added dropwise to the reaction mixture by a separatory funnel. After the completion of the dropwise addition, the reaction mixture was heated at 50° C. for 4 hours. Thin layer chromatography was used to track the reaction to completion, heating was stopped, and the protective device was removed. The reaction mixture was concentrated, washed with water, and extracted with ethyl acetate. Ethyl acetate was concentrated and dried to obtain a crude product. The crude product was purified by silica gel column chromatography with petroleum ether/ethyl acetate=2:1 as eluent, and the eluent was concentrated under reduced pressure and dried to obtain 203.3 mg of the title compound, a yield of 64.58%.

EXAMPLE 3

Preparation of Compound of Formula (I)

In a 100 mL three-necked flask, 246.0 mg (0.65 mmol) of pleuromulin and 6.1 mg (0.06 mmol) triethylamine were dissolved in 20 mL of toluene, under nitrogen atmosphere. 121.7 mg (0.78 mmol) of salicyloyl chloride (compound of formula III) was dissolved in 20 mL of toluene, and added dropwise to the reaction mixture by a separatory funnel. After the completion of the dropwise addition, the reaction mixture was heated at 30° C. for 6 hours. Thin layer chromatography was used to track the reaction to completion, heating was stopped, and the protective device was removed. The reaction mixture was concentrated, washed with water, and extracted with ethyl acetate. Ethyl acetate was concentrated and dried to obtain a crude product. The crude product was purified by silica gel column chromatography with petroleum ether/ethyl acetate=1:1 as eluent, and the eluent was concentrated under reduced pressure and dried to obtain 210.1 mg of the title compound, a yield of 66.75%.

EXAMPLE 4

Preparation of Compound of Formula (I)

In a 100 mL three-necked flask, 246.0 mg (0.65 mmol) of pleuromulin and 6.1 mg (0.06 mmol) triethylamine were dissolved in 20 mL of dichloromethane under nitrogen atmosphere. 132.6 mg (0.85 mmol) of salicyloyl chloride (compound of formula III) was dissolved in 10 mL of dichloromethane, and added dropwise to the reaction mixture by a separatory funnel. After the completion of the dropwise addition, the reaction mixture was heated at 20° C. for 8 hours. Thin layer chromatography was used to track the reaction to completion, heating was stopped, and the protective device was removed. The reaction mixture was concentrated, washed with water, and extracted with ethyl acetate. Ethyl acetate was concentrated and dried to obtain a crude product. The crude product was purified by silica gel column chromatography with petroleum ether/ethyl acetate=1:1 as eluent, and the eluent was concentrated under reduced pressure and dried to obtain 201.0 mg of the title compound, a yield of 63.85%.

EXAMPLE 5

Preparation of Compound of Formula (I)

In a 100 mL three-necked flask, 246.0 mg (0.65 mmol) of pleuromulin and 6.1 mg (0.06 mmol) triethylamine were dissolved in 20 mL of N,N-dimethylformamide, under nitrogen atmosphere. 112.3 mg (0.72 mmol) of salicyloyl chloride (compound of formula III) was dissolved in 10 mL of N,N-dimethylformamide, and added dropwise to the reaction mixture by a separatory funnel. After the completion of the dropwise addition, the reaction mixture was heated at 40° C. for 7 hours. Thin layer chromatography was used to track the reaction to completion, heating was stopped, and the protective device was removed. The reaction mixture was concentrated, washed with water, and extracted with ethyl acetate. Ethyl acetate was concentrated and dried to obtain a crude product. The crude product was purified by silica gel column chromatography with petroleum ether/ethyl acetate=1:1 as eluent, and the eluent was concentrated under reduced pressure and dried to obtain 196.9 mg of the title compound, a yield of 62.56%.

EXAMPLE 6

Preparation of Compound of Formula (I)

In a 100 mL three-necked flask, 246.0 mg (0.65 mmol) of pleuromulin and 6.1 mg (0.06 mmol) triethylamine were dissolved in 20 mL of dichloromethane under nitrogen atmosphere. 121.7 mg (0.78 mmol) of salicyloyl chloride (compound of formula III) was dissolved in 10 mL of dichloromethane, and added dropwise to the reaction mixture by a separatory funnel. After the completion of the dropwise addition, the reaction mixture was heated at 45° C. for 5 hours. Thin layer chromatography was used to track the reaction to completion, heating was stopped, and the protective device was removed. The reaction mixture was concentrated, washed with water, and extracted with ethyl acetate. Ethyl acetate was concentrated and dried to obtain a crude product. The crude product was purified by silica gel column chromatography with petroleum ether/ethyl acetate=2:1 as eluent, and the eluent was concentrated under reduced pressure and dried to obtain 194.8 mg of the title compound, a yield of 61.89%.

EXAMPLE 7

Preparation of Compound of Formula (I)

In a 100 mL three-necked flask, 246.0 mg (0.65 mmol) of pleuromulin and 6.1 mg (0.06 mmol) triethylamine were dissolved in 20 mL of toluene, under nitrogen atmosphere. 112.3 mg (0.72 mmol) of salicyloyl chloride (compound of formula III) was dissolved in 20 mL of toluene, and added dropwise to the reaction mixture by a separatory funnel. After the completion of the dropwise addition, the reaction mixture was heated at 40° C. for 7 hours. Thin layer chromatography was used to track the reaction to completion, heating was stopped, and the protective device was removed. The reaction mixture was concentrated, washed with water, and extracted with ethyl acetate. Ethyl acetate was concentrated and dried to obtain a crude product. The crude product was purified by silica gel column chromatography with petroleum ether/ethyl acetate=3:1 as eluent, and the eluent was concentrated under reduced pressure and dried to obtain 199.7 mg of the title compound, a yield of 63.43%.

EXAMPLE 8

Preparation of Compound of Formula (I)

In a 100 mL three-necked flask, 246.0 mg (0.65 mmol) of pleuromulin and 6.1 mg (0.06 mmol) triethylamine were dissolved in 20 mL of dichloromethane under nitrogen atmosphere. 121.7 mg (0.78 mmol) of salicyloyl chloride (compound of formula III) was dissolved in 10 mL of dichloromethane, and added dropwise to the reaction mixture by a separatory funnel. After the completion of the dropwise addition, the reaction mixture was heated at 50° C. for 5 hours. Thin layer chromatography was used to track the reaction to completion, heating was stopped, and the protective device was removed. The reaction mixture was concentrated, washed with water, and extracted with ethyl acetate. Ethyl acetate was concentrated and dried to obtain a crude product. The crude product was purified by silica gel column chromatography with petroleum ether/ethyl acetate=1:1 as eluent, and the eluent was concentrated under reduced pressure and dried to obtain 210.0 mg of the title compound, a yield of 66.71%.

EXAMPLE 9

Preparation of Compound of Formula (I)

In a 100 mL three-necked flask, 246.0 mg (0.65 mmol) of pleuromulin and 6.1 mg (0.06 mmol) triethylamine were dissolved in 20 mL of toluene, under nitrogen atmosphere. 121.7 mg (0.78 mmol) of salicyloyl chloride (compound of formula III) was dissolved in 20 mL of toluene, and added dropwise to the reaction mixture by a separatory funnel. After the completion of the dropwise addition, the reaction mixture was heated at 35° C. for 6 hours. Thin layer chromatography was used to track the reaction to completion, heating was stopped, and the protective device was removed. The reaction mixture was concentrated, washed with water, and extracted with ethyl acetate. Ethyl acetate was concentrated and dried to obtain a crude product. The crude product was purified by silica gel column chromatography with petroleum ether/ethyl acetate=2:1 as eluent, and the eluent was concentrated under reduced pressure and dried to obtain 189.4 mg of the title compound, a yield of 60.18%.

EXAMPLE 10

Preparation of Compound of Formula (I)

In a 100 mL three-necked flask, 246.0 mg (0.65 mmol) of pleuromulin and 6.1 mg (0.06 mmol) triethylamine were dissolved in 20 mL of toluene, under nitrogen atmosphere. 101.4 mg (0.65 mmol) of salicyloyl chloride (compound of formula III) was dissolved in 20 mL of toluene, and added dropwise to the reaction mixture by a separatory funnel. After the completion of the dropwise addition, the reaction mixture was heated at 20° C. for 7 hours. Thin layer chromatography was used to track the reaction to completion, heating was stopped, and the protective device was removed. The reaction mixture was concentrated, washed with water, and extracted with ethyl acetate. Ethyl acetate was concentrated and dried to obtain a crude product. The crude product was purified by silica gel column chromatography with petroleum ether/ethyl acetate=1:1 as eluent, and the eluent was concentrated under reduced pressure and dried to obtain 196.6 mg of the title compound, a yield of 62.45%.

EXAMPLE 11

Preparation of Compound of Formula (I)

In a 100 mL three-necked flask, 246.0 mg (0.65 mmol) of pleuromulin and 6.1 mg (0.06 mmol) triethylamine were dissolved in 20 mL of dichloromethane under nitrogen atmosphere. 112.3 mg (0.72 mmol) of salicyloyl chloride (compound of formula III) was dissolved in 10 mL of dichloromethane, and added dropwise to the reaction mixture by a separatory funnel. After the completion of the dropwise addition, the reaction mixture was heated at 35° C. for 4 hours. Thin layer chromatography was used to track the reaction to completion, heating was stopped, and the protective device was removed. The reaction mixture was concentrated, washed with water, and extracted with ethyl acetate. Ethyl acetate was concentrated and dried to obtain a crude product. The crude product was purified by silica gel column chromatography with petroleum ether/ethyl acetate=1:1 as eluent, and the eluent was concentrated under reduced pressure and dried to obtain 203.2 mg of the title compound, a yield of 64.56%.

EXAMPLE 12

Preparation of Compound of Formula (I)

In a 100 mL three-necked flask, 246.0 mg (0.65 mmol) of pleuromulin and 6.1 mg (0.06 mmol) triethylamine were dissolved in 20 mL of dichloromethane under nitrogen atmosphere. 1122.3 mg (0.72 mmol) of salicyloyl chloride (compound of formula III) was dissolved in 10 mL of dichloromethane, and added dropwise to the reaction mixture by a separatory funnel. After the completion of the dropwise addition, the reaction mixture was heated at 30° C. for 6 hours. Thin layer chromatography was used to track the reaction to completion, heating was stopped, and the protective device was removed. The reaction mixture was concentrated, washed with water, and extracted with ethyl acetate. Ethyl acetate was concentrated and dried to obtain a crude product. The crude product was purified by silica gel column chromatography with petroleum ether/ethyl acetate=1:2 as eluent, and the eluent was concentrated under reduced pressure and dried to obtain 199.9 mg of the title compound, a yield of 63.50%.

EXAMPLE 13

Preparation of Compound of Formula (I)

In a 250 mL three-necked flask, 246.0 mg (0.65 mmol) of pleuromulin , 99.4 mg (0.72 mmol) of salicylic acid and 12.0 mg (0.007 mmol) silicomolybdic acid were dissolved in 100 mL of 1-Butyl-3-methylimidazolium tetrafluoroborate , and nitrogen gas was added thereto. After full dissolution, the temperature was raised to 25° C. and the reaction was carried out for 3 hours. Thin layer chromatography was used to track the reaction to completion, heating was stopped, and the protective device was removed. The reaction mixture system was allowed to separate into layers to give a crude pleuromulin salicylic acid ester. The crude product was recrystallized with 30 mL methanol and dried to obtain pleuromulin salicylic acid ester. The derivative was 269.7 mg, and the total yield was 85.69%.

EXAMPLE 14

Preparation of Compound of Formula (I)

In a 250 mL three-necked flask, 246.0 mg (0.65 mmol) of pleuromulin, 99.4 mg (0.72 mmol) of salicylic acid and 12.0 mg (0.007 mmol) silicomolybdic acid were dissolved in 100 mL of 1-butyl-3-methylimidazolium tetrafluoroborate under nitrogen atmosphere. After full dissolution, the reaction mixture was heated at 20° C. for 5 hours. Thin layer chromatography was used to track the reaction to completion, heating was stopped, and the protective device was removed. The reaction mixture was allowed to separate into layers to obtain a crude product. The crude product was recrystallized with 30 mL methanol and dried to obtain 256.6 mg of the titled compound, a yield of 81.53%. 1-Butyl-3-methylimidazolium tetrafluoroborate was recovered.

EXAMPLE 15

Preparation of Compound of Formula (I)

In a 250 mL three-necked flask, 246.0 mg (0.65 mmol) of pleuromulin, 99.4 mg (0.72 mmol) of salicylic acid and 12.0 mg (0.007 mmol) silicomolybdic acid were dissolved in 100 mL of 1-octyl-3-methylimidazolium hexafluorophosphate under nitrogen atmosphere. After full dissolution, the reaction mixture was heated at 40° C. for 4 hours. Thin layer chromatography was used to track the reaction to completion, heating was stopped, and the protective device was removed. The reaction mixture was allowed to separate into layers to obtain a crude product. The crude product was recrystallized with 30 mL methanol and dried to obtain 250.5 mg of the titled compound, a yield of 79.58%. 1-Octyl-3-methylimidazolium hexafluorophosphate was recovered.

EXAMPLE 16

Preparation of Compound of Formula (I)

In a 250 mL three-necked flask, 246.0 mg (0.65 mmol) of pleuromulin, 99.4 mg (0.72 mmol) of salicylic acid and 12.0 mg (0.007 mmol) silicomolybdic acid were dissolved in 100 mL of 1-hexyl-3-methylimidazolium tetrafluoroborate under nitrogen atmosphere. After full dissolution, the reaction mixture was heated at 35° C. for 4 hours. Thin layer chromatography was used to track the reaction to completion, heating was stopped, and the protective device was removed. The reaction mixture was allowed to separate into layers to obtain a crude product. The crude product was recrystallized with 30 mL methanol and dried to obtain 243.3 mg of the titled compound, a yield of 77.31%. 1-Hexyl-3-methylimidazolium tetrafluoroborate was recovered.

EXAMPLE 17

Antibacterial Activity Test of the Compounds of the Invention

The antimicrobial efficacy was determined by a paper diffusion method drug sensitivity test.

E Experimental strains: multi-resistant *Staphylococcus aureus* 206 (MRSA-206), multi-resistant *Staphylococcus aureus* 575 (MRSA-575), multi-resistant *Staphylococcus aureus* 596 (MRSA-596). The experimental strain was identified by Huashan Hospital Affiliated to Fudan University (Institute of Antibiotic of Fudan University).

Drug sensitive paper: The drug sensitive paper was a special drug sensitive paper with a diameter of 6.35 mm and a water absorption of 0.02 mL. The control drug was vancomycin (30 µg/tablet); the test drugs were pleuromulin (30 µg/tablet), salicylic acid (30 µg/tablet) and pleuromulin salicylic acid ester (30 µg/tablet).

Reagents: LB agar medium, LA broth medium, 0.5% DMSO solution.

Equipment: Ultra-clean workbench, high-pressure sterilization pot, gas bath constant temperature shaking incubator.

Preparation of bacterial suspension:

T The experimental strains were inoculated in non-selective medium and placed in air at 37° C. for 24 h. A single colony that grows well and inoculate it into broth medium was incubate at 35° C.±2° C. for 6 hours, and LA broth medium was used to calibrate the concentration of the bacterial solution to 0.5 Mie turbidimetric tube ($1.5 \times 10^8$ CFU/mL). A bacterial suspension was obtained.

Paper diffusion method drug sensitivity test:

LB dry powder was weighed, sterilized at 103.4 Kpa, 121.3° C. high-pressure steam for 15 min, and then placed it in a 40° C.-50° C. water bath. A sterile empty plate (inner diameter 9 cm) was placed on the surface of the ultra-clean table water table, and LB dry powder was poured to the plate. The thickness of each plate was 3 mm to 4 mm. After the plate was cooled at room temperature, it was stored in the refrigerator at 2° C.-8° C. A sterile cotton swab was used to dip the bacterial solution and ti evenly coat the surface of the LB plate 3 times. After inoculation of the bacterial suspension, the LB plate was dried at room temperature for 3 min to 5 min. Sterile forceps were used to closely attach the antibacterial drug paper to the dish. The dish was put upside down and placed in a 37° C. incubator for 24 h. The results were observed by measuring the diameter. Taking 0.5% DMSO solution as a negative control, the antibacterial activity is expressed by the diameter of the inhibition zone. The inhibition zone≥17 mm, sensitive; the inhibition zone of 15 mm-16 mm, intermediary; the inhibition zone≤14 mm, drug resistance.

Figure 2:
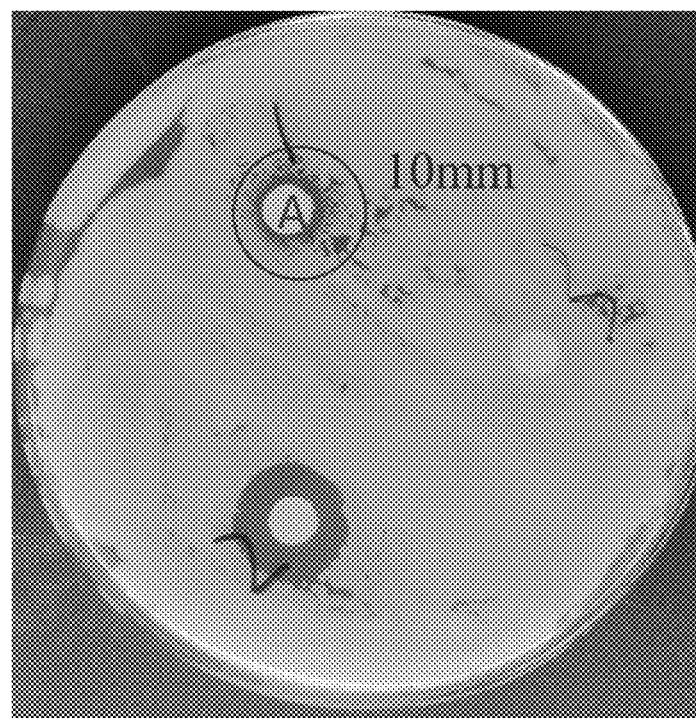
FIG. 2 shows the in vitro antibacterial activity of pleuromulin salicylic acid ester against drug-resistant bacteria MARS 18-575.
Figure 3:
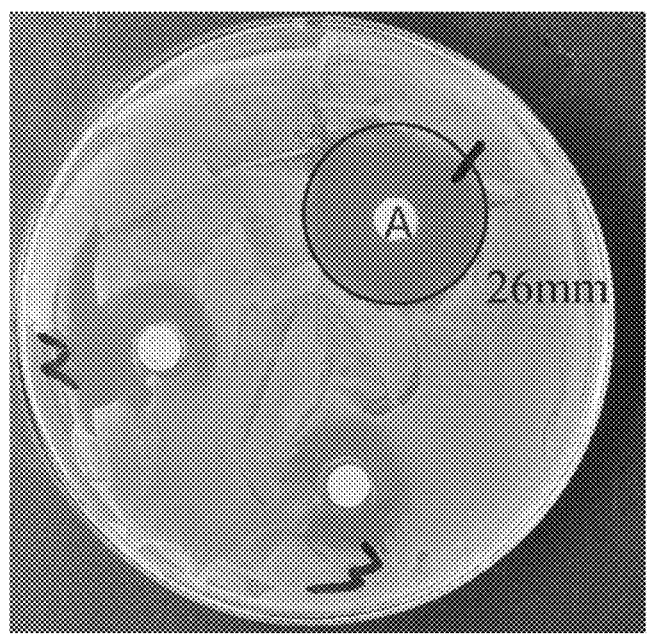
FIG. 3 shows the in vitro antibacterial activity of pleuromulin salicylic acid ester against drug-resistant bacteria MARS 18-596.

In FIGS. 1-3, pleuromulin salicylic acid ester is represented by the letter A. FIG. 1 shows the antibacterial effect of the pleuromulin salicylic acid ester on MRSA-206.

FIG. 2 shows the antibacterial effect of the pleuromulin salicylic acid ester on MRSA-575. FIG. 3 shows the antibacterial effect of the pleuromulin salicylic acid ester on MRSA-596. The results are shown in Table 1.

TABLE 1

Experimental results of the zone of inhibition

| Compound | Zone of inhibition /mm Strain | | |
|---|---|---|---|
| | MRSA-171 | MRSA-575 | MRSA-596 |
| 0.5% DMSO | 0 | 0 | 0 |
| Vancomycin | 15 | 17 | 23 |
| Pleuromulin | 0 | 0 | 0 |
| Salicylic acid | 0 | 0 | 0 |
| Pleuromulin salicylic acid ester | 16 | 10 | 26 |

The results in FIGS. 1-3 and Table 1 show that the starting materials pleuromutilin and salicylic acid have no inhibitory effect on drug-resistant bacteria. Pleuromutilin salicylic acid has strong inhibitory effects on multi-drug resistant *Staphylococcus aureus* 171, 575, 596, and the diameter of bacteriostatic zone against multidrug resistant *Staphylococcus aureus* 596 was up to 26 mm. In summary, the pleuromutilin salicylic acid ester of the present invention can be used as an antibacterial drug candidate for multi-drug resistant *Staphylococcus aureus*.

What is claimed is:

1. A compound having the following formula (I):

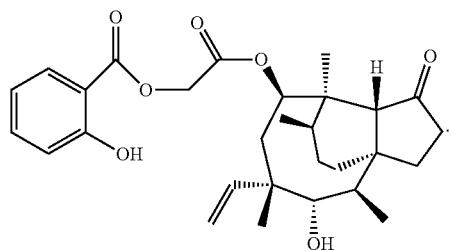

2. A method of preparing the compound of formula (I) of claim 1, comprising:
reacting a compound of formula (II) with a compound of formula (III) to obtain the compound of formula (I):

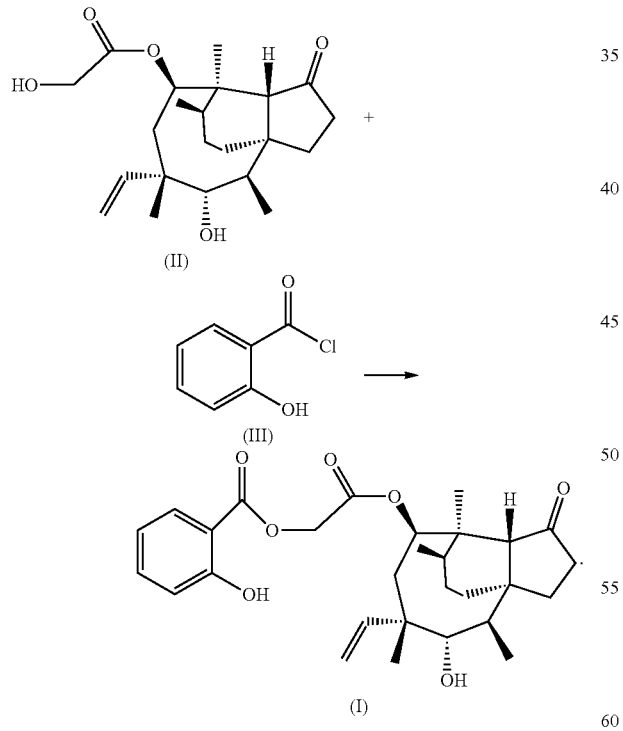

3. The method of claim 2, wherein the reaction of the compound of formula (II) with the compound of formula (III) comprises the following steps:
placing the compound of formula (II) and the compound of formula (III), in a molar ratio of 1:1 to 1:1.3, in a reactor;
adding an organic solvent and a catalytic amount of triethylamine under a nitrogen atmosphere to obtain a reaction mixture;
heating the reaction mixture at 20-50° C. for 4-8 hours;
concentrating the reaction mixture and extracting with ethyl acetate to obtain a crude product; and
purifying the crude product on a fresh silica gel chromatography column with petroleum ether and ethyl acetate as an eluent to obtain the compound of formula (I).

4. The method of claim 3, wherein the organic solvent is toluene, dichloromethane, or N,N-dimethylformamide.

5. The method of claim 4, wherein the organic solvent is dichloromethane.

6. The method of claim 3, wherein the molar ratio of the compound of formula (II) and the compound of formula (III) is 1:1.1.

7. The method of claim 3, wherein the reaction mixture is heated at 20° C.

8. The method of claim 3, wherein the reaction mixture is heated for 5 hours.

9. A method of preparing the compound of formula (I) of claim 1, comprising:
reacting a compound of formula (II) with a compound of formula (IV) to obtain the compound of formula (I):

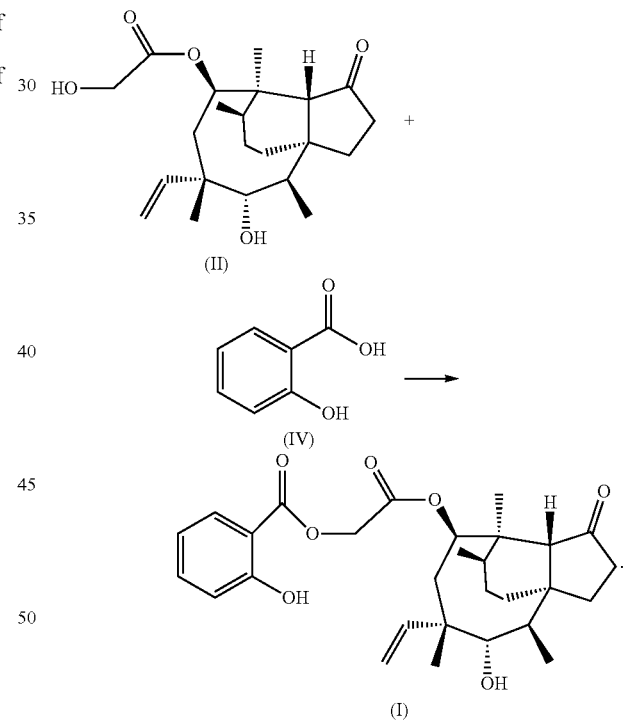

10. The method of claim 9, wherein the reaction of the compound of formula (II) with the compound of formula (IV) comprises the following steps:
placing the compound of formula (II), a catalyst, and an ionic liquid in a reactor under a nitrogen atmosphere, the catalyst being 12-molybdosilicic acid hydrate of formula $H_6Mo_{12}O_{41}Si$;
adding the compound of formula (IV) to the reactor to form a reaction mixture;
heating the reaction mixture at 20-40° C. for 2-5 hours;
placing the reaction mixture in a separating funnel to separate a crude product;

purifying the crude product by recrystallization in methanol to obtain the compound of formula (I); and
recycling the ionic liquid.

11. The method of claim 10, wherein the ionic liquid is 1-octyl-3-methylimidazolium hexafluorophosphate, 1-hexyl-3-methylimidazolium tetrafluoroborate, or 1-butyl-3-methylimidazolium tetrafluoroborate.

12. The method of claim 10, wherein the ionic liquid is 1-octyl-3-methylimidazolium hexafluorophosphate.

13. The method of claim 10, wherein the compound of formula (II) and the compound (IV) have a molar ratio of 1:1 to 1:1.3.

14. The method of claim 13, wherein the molar ratio of the compound of formula (II) and the compound of formula (IV) is 1:1.1.

15. The method of claim 10, wherein the reaction mixture is heated at 25° C.

16. The method of claim 10, wherein the reaction mixture is heated for 3 hours.

* * * * *